United States Patent
Balian (10) Patent No.: US 12,412,664 B2
(45) Date of Patent: Sep. 9, 2025

(54) ADDICTION PREDICTOR AND RELAPSE DETECTION SUPPORT TOOL

(71) Applicant: CERNER INNOVATION, INC., Kansas City, KS (US)

(72) Inventor: Richard Matthew Balian, Birdsboro, PA (US)

(73) Assignee: Cerner Innovation, Inc., Kansas City, MO (US)

( * ) Notice: Subject to any disclaimer, the term of this patent is extended or adjusted under 35 U.S.C. 154(b) by 1218 days.

(21) Appl. No.: 16/452,220

(22) Filed: Jun. 25, 2019

(65) Prior Publication Data

US 2020/0411191 A1 Dec. 31, 2020

(51) Int. Cl.
| | | |
|---|---|---|
| G06F 16/00 | (2019.01) | |
| G06F 16/245 | (2019.01) | |
| G06N 5/02 | (2023.01) | |
| G16H 10/60 | (2018.01) | |
| G16H 50/30 | (2018.01) | |

(52) U.S. Cl.
CPC ........... *G16H 50/30* (2018.01); *G06F 16/245* (2019.01); *G06N 5/02* (2013.01); *G16H 10/60* (2018.01)

(58) Field of Classification Search
CPC ...... G16H 50/30; G16H 10/60; G06F 16/245; G06N 5/02
See application file for complete search history.

(56) References Cited

U.S. PATENT DOCUMENTS

| | | | |
|---|---|---|---|
| 7,181,375 B2 | 2/2007 | Rao et al. | |
| 2010/0269157 A1* | 10/2010 | Experton | G06F 21/6245 726/28 |
| 2011/0295621 A1 | 12/2011 | Farooq et al. | |
| 2012/0173264 A1 | 7/2012 | Brush et al. | |
| 2013/0086163 A1 | 4/2013 | Neff | |
| 2014/0095201 A1 | 4/2014 | Farooq et al. | |
| 2015/0039343 A1* | 2/2015 | Cline | G16H 10/60 705/3 |
| 2015/0064672 A1 | 3/2015 | Bars | |
| 2017/0177801 A1 | 6/2017 | Ryan et al. | |
| 2018/0174673 A1* | 6/2018 | DeFrank | G16H 50/30 |
| 2018/0181713 A1 | 6/2018 | Pillarisetty et al. | |
| 2018/0181719 A1 | 6/2018 | Balian | |
| 2019/0385259 A1* | 12/2019 | Tayal | G06Q 30/02 |
| 2020/0118458 A1* | 4/2020 | Shriberg | G16H 50/20 |
| 2020/0145210 A1* | 5/2020 | Thekadath | H04L 9/3239 |

* cited by examiner

*Primary Examiner* — Alex Gofman
*Assistant Examiner* — Suman Rajaputra
(74) *Attorney, Agent, or Firm* — Invoke (57) ABSTRACT

Technologies are provided for predicting an individual's likelihood of addiction or relapse to pharmaceuticals that include controlled or addictive substances. The prediction can be used to generate an alert that, in some aspects, prevents care provider actions in an electronic health record system that are related to the addictive pharmaceutical until the prediction is acknowledged. Further, the data used as input in the predictive modeling can be disassociated from the prediction after the prediction is generated.

25 Claims, 5 Drawing Sheets

ADDICTION PREDICTOR AND RELAPSE DETECTION SUPPORT TOOL

BACKGROUND

Addiction is a primary, chronic disease of brain reward, motivation, memory, and related phenomena. Abnormality in these functions leads to characteristic biological, psychological, social, and spiritual manifestations. This is reflected in an individual pathologically pursuing reward or relief by substance use and other behaviors. Addiction is characterized by inability to consistently abstain, impairment in behavioral control, craving, diminished recognition of significant problems with one's behaviors and interpersonal relationships, and a dysfunctional emotional response.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Pharmacological advancements have created numerous beneficial medications that can relieve pain, combat depression, lower blood pressure, or balance neurochemistry amongst a plethora of other physiologic and psychologic benefits. However, addiction to medications (such as opioids, barbiturates, benzodiazepines, phenidates, amphetamines, and other controlled substances) can be as destructive to a person as the medication's therapeutic use can be beneficial. While the most destructive consequence of addiction may be the death of the person or someone else, other common effects of addiction can include impaired behavioral control, craving, diminished recognition of significant problems with one's behaviors and interpersonal relationships, and dysfunctional emotional responses, among other things.

In some cases, addiction to controlled substances begins with a medically valid and legitimately acquired prescription to a pharmaceutical containing the controlled substance. For example, a teenager may be injured while participating in athletics and may, appropriately, be prescribed an opioid to manage pain associated with the injury. When the first prescription is consumed or during a follow up appointment, the teenager may legitimately (or illegitimately) request additional medication. Or, the care provider may perceive the teenager is still in pain and offer a refill of the prescription, a similar pharmaceutical, or a change in dosage. Or, the teenager's guardian may perceive the teenager is still in pain and request the same. In any case, during recovery the teenager can gradually develop a dependence on the pharmaceutical (e.g., the opioid in this case) and at some point addiction sets in. The teenager's life is detrimentally altered and the youthful potential possibly destroyed. For another example, a combat veteran may have physical or psychological injuries that necessitate and deserve long term treatment regimes. Upon returning to civilian life, the veteran can be prescribed multiple pharmaceuticals that are potentially addictive. Like the teenager, the veteran can gradually develop an addiction. However, differences between the types of the injury, differences in expected treatment duration, and experiential differences between the veteran and the teenager can materially alter the probability of addiction.

On an individual basis, the effects of addiction are tragic. On a societal level the expenditure of healthcare resources treating addiction and relapse of an increasingly large number of people can alter the availability and quality of care for everyone. Unfortunately, the gradual deterioration of a patient from legitimate therapeutic use through initial dependence to addiction creates unique prediction, detection, and prevention problems that may not be addressed by the traditional electronic health record (EHR) systems used in the healthcare system. For example, although traditional EHR systems record health data for patients over time, a mere record of discrete instances of patient contact is often insufficient to distinguish a potential case of addiction from normal variations in a patient. While a chart review, or a general review of a patient's history may sufficiently address a yearly check-up or emergency room visit, even an in-depth review of a patient's prescription history and an initial complaint may not distinguish "drug seeking behavior" (e.g., potential addiction issues) from a series of unconnected legitimate pharmacological interventions. Thus, traditional EHR systems can be incapable of identifying data that may be crucial to a care provider when they are choosing treatment options. Conversely, another limitation of traditional EHR systems can be thought of as an informational overload problem. Said another way, some traditional EHR systems attempt to solve the EHR's inability to identify pertinent patient information by providing the care provider every piece of patient information held in the EHR, overwhelming a care provider's analytical ability in an ocean of irrelevant information.

Further, the proliferation of urgent care, surgi-centers, rehabilitation clinics, satellite care centers, and other public or private clinics means that patients often interact with multiple care providers across multiple institutions. These institutions commonly structure the data within their respective EHR systems differently from other institutions (e.g., the organization of a database table, the subsystem that maintains a record(s), the programmatic language, and so forth), use different versions of the EHR system at different locations (e.g., a community clinic using a "lite" or older version while the level 3 trauma center in the heart of the city uses the newest iteration), or have different data formatting procedures (e.g., including/omitting middle initials, month/day/year or year/month/day, including/omitting a unit identifier, metric/imperial). These differences mean that identifying and collecting patient information across multiple disparate traditional EHR systems can be prevented based on incompatibilities between the sources of patient data.

Further, traditional predictive techniques can maintain traceability between input data and a predictive models output. This traceability can have benefits during model development. However, traceability also allows post-hoc rationalization of the model's output. For example, a target patient, the care provider, or a target patient's guardian(s) may attempt to explain away traditional predictive model outputs. Alternatively, traceability can enable a target patient to intentionally alter or attempt to alter the data that is provided to a traditional model. Thereby skewing the output in a manner that inhibits the accuracy of traditional models.

Accordingly, the embodiments described herein, at least partially, prevent situations like those mentioned above from occurring through improvements to current electronic health record (EHR) system technology. For example, some embodiments described herein predict the likelihood of pharmaceutical addiction or relapse for a target patient. An example embodiment comprises a method for automatically predicting the likelihood of addiction for an individual based on a predictive model that includes accessing a predictive model having a plurality of input variables, retrieving a plurality of sets of structured data via at least one application programming interface, wherein each set of structured data of the plurality of sets of structured data is retrieved from a remote disparate database, and extracting from each retrieved set of structured data a set of input variables. The method can further include automatically standardizing the set input variables, using a pre-model transformation to generate standardized input variables and utilizing the predictive model and the standardized input variables to determine a prediction for a likelihood of addiction for the individual. Additionally, the method includes detecting an access request for the individual's electronic health record (EHR) by a caregiver via a computing device networked with a remote health record server maintaining the individual's EHR and in response to detecting the access request for the individual's electronic health record (EHR), providing the determined likelihood of addiction for presentation to the caregiver via the computing device. An access request can include creation of a prescription for the individual by the caregiver via the computing device networked with the remote health record server. In some embodiments, the creation of a prescription automatically triggers presentation of an alert that prevents completion of the prescription for the individual until manually acknowledged by the caregiver via the computing device networked with the remote health record server. Further, some embodiments of the method also include disassociating the standardized input variables and the retrieved set input variables disassociated from the prediction for the likelihood of addiction and the individual's EHR. For another example, some embodiments described herein predict the likelihood of a relapse in a patient with a prior history of addiction.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

A system, as used herein, refers to any device, process, or service or combination thereof. As used herein, engine is synonymous with system unless otherwise stated. A system may be implemented using components or generators as hardware, software, firmware, a special-purpose device, or any combination thereof. A system may be integrated into a single device or it may be distributed over multiple devices. The various components or generators of a system may be co-located or distributed. For example, although discussed for clarity as the prediction engine, operations discussed may be performed in a distributed manner. The system may be formed from other systems and components thereof. It should be understood that this and other arrangements described herein are set forth only as examples.

Figure 1:
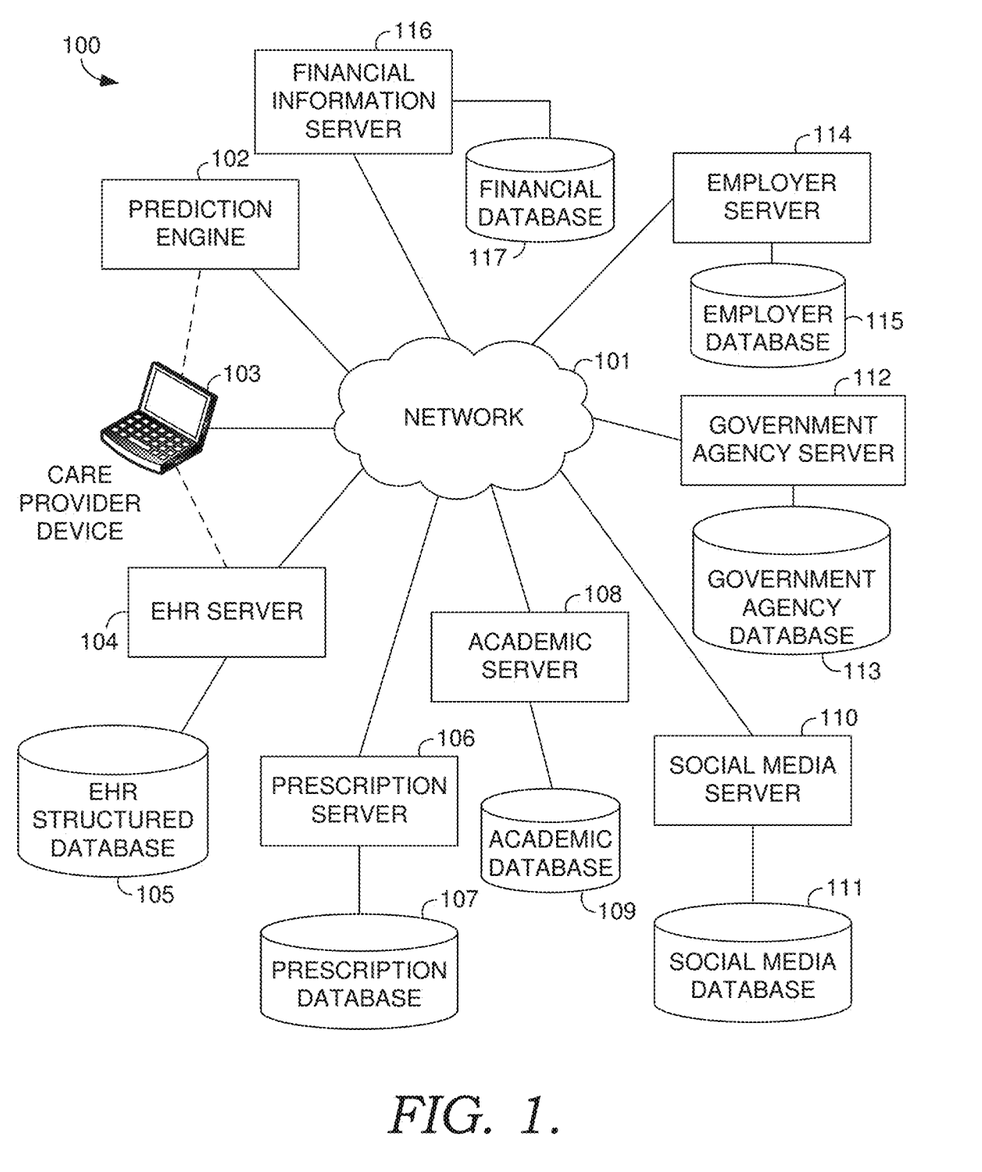
FIG. 1 depicts an exemplary operating environment consistent with embodiments described herein.

Turning to FIG. 1, an example operating environment 100 suitable for practicing embodiments of the invention is depicted. In particular, FIG. 1 shows a high level architecture of operating environment 100 having components in accordance with implementations of the present disclosure. Generally, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Example operating environment 100 includes a computerized system for compiling and running an embodiment of a decision support recommendation service, such as prediction engine 102. Prediction engine 102 generally facilitates acquisition of structured and unstructured data from one or more disparate data sources relevant to the prediction of a patient's likelihood of addiction or relapse. By way of example, the prediction engine 102 may include an application programming interface (API) library that includes specifications for routines, data structures, object classes, and variables that support the interaction of the prediction engine 102 architecture and the software framework of the disparate data sources (e.g., electronic health record server 104, prescription record server 106, academic record server 108, social media server 110, government agency record server 112, employer record server 114, and so forth). As described in more detail in relation to data source interface 201 of FIG. 2, these APIs include configuration specifications for the prediction system such that the components therein may communicate with each other, as described herein.

Further, embodiments of the prediction engine 102 facilitate analysis of structured and unstructured data to generate a prediction of a patient's likelihood of addiction or relapse. As part of the analysis the prediction engine 102 can extract variables from the structured and unstructured data maintained by remote servers, local servers, or both. For example, the prediction engine 102 can invoke natural language processing algorithms to identify relevant variables in unstructured free text stored in a database maintained by one or more of the disparate data sources. For another example, the prediction engine 102 can invoke synonymic discovery algorithms to index or map variables in records and map ontologies present in the disparate data sources.

Some embodiments of operating environment 100 also include one or more care provider device(s) 103. Care provider device 103 can include any device, such as those described in relation to FIG. 5, that facilitates access to an EHR for one or more patients maintained by EHR server 104. For example, care provider device 103 can include a workstation, laptop, desktop, tablet, smart phone, mobile workstation, or any other computing device communicatively coupled to EHR server 104.

Some embodiments of operating environment 100 also include electronic health record server 104, prescription record server 106, academic record server 108, social media server 110, government agency record server 112, employer record server 114, or any combination thereof. In some embodiments, each server can have a data structure disparate from every other server. In some embodiments, at least one server can share a data structure with at least one other server. For example, the organization or internal references of a database table maintained by a first server (e.g., electronic health record server 104) can differ from the organization or internal references of a database table maintained by a second server (e.g. government agency record server 112).

Electronic health record (EHR) server 104 maintains, and provides access to, one or more EHR database(s) 105 containing records of treatment events, medication history, substance use history, demographic attributes, laboratory tests, time and date data, any other health related data, or any combination thereof for a plurality of patients. For example, EHR database 105 can include GC/MS results for THC, THC metabolites, opioids, opioid metabolites (e.g., the metabolites of heroin, opium, morphine, hydrocodone, oxycodone, and so forth), and other pharmaceuticals or metabolites thereof. Additionally, EHR database 105 can include clinical notes, appointment notes, records of issued prescriptions, diagnoses, care plans, bloodwork, urinalysis, respiratory data, and treatment data for each patient of a healthcare institution or a plurality of healthcare institutions. Further, EHR database 105 can include images, representations, or clinical documentation of burns, needle marks or unexplained abrasions, shakes/tremors, lack of personal hygiene, scars, unsubstantiated pains, requests for opioids or pain medication, etc. Additionally, in some embodiments, the EHR server 104 can maintain one or more pharmaceutical formularies that identify the chemical composition of pharmaceuticals prescribed by, or available for prescription by, care providers. The formularies can further include keywords, potential for addiction information, dosage guidelines, generic and non-generic names, national drug codes (NDC), and any other data related to prescribeable pharmaceuticals. In some embodiments, a specific potential-for-addiction formulary can include a subset of pharmaceuticals with a known potential for abuse or addiction.

Prescription record server 106 maintains, and provides access to, one or more prescription database(s) 107 containing records of patient prescriptions submitted to a pharmacy. For example, prescription database 107 can include: images of digital or physical prescriptions; the name of the patient; the name of the prescribing care provider; the commercial name of the pharmaceutical; the generic name of the pharmaceutical; the number of refills authorized/dispensed/remaining; the amount and dosage of the pharmaceutical; any usage notes (e.g., "take 2 pills every three hours", "PO BID", and so forth); date submitted; date(s) filled; location of pharmacy; payment method; insurance provider; or any other relevant prescription information. Additionally, prescription record server 106 can exchange data with other prescription record servers (not depicted). For example, prescription record server 106 continuously, periodically, intermittently, or upon request transmits a record update request to another prescription record server(s) associated with a different entity, geographic region, or network. In response, prescription record server 106 is provided access to or otherwise receives any records of patient prescriptions submitted to the pharmacies associated with the other prescription record server that are not already stored in prescription database 107.

Academic record server 108 maintains, and provides access to, one or more academic database(s) 109 containing a patient's school records. For example, academic database 108 can include a patient's GPA; attendance records; social and disciplinary notes; teacher feedback; school related activities such as sports, academic clubs/teams, social clubs; or any other academic data related to a patient.

Social media server 110 maintains, and provides access to, one or more social media database(s) 111 containing a patient's activity in/on one or more social media platforms. For example, social media database 111 can include text and image posts, keyword tags (such as hashtags), relationships (e.g., connections between the patient and any other member of the social media platform), activity (e.g., login locations, times, device identity, and so forth), actions (e.g., like(s), re-posts, replies, and so forth), or any other social media data related to a patient. Examples of social media server 110 include the servers of Facebook®, Instagram®, LinkedIn®, Twitter®, and so forth.

Government agency record server 112 maintains, and provides access to, one or more governmental agency database(s) 113. For example, one or more government agency record servers 112 can maintain military personnel records, police arrest records and statistics, emergency medical response records (e.g., ambulance callouts) and statistics, or any other government record for a patient or the population of the region. Examples of government agency record server 112 include the servers of the Bureau of Justice Statistics, National Incident-Based Reporting System, National Criminal Justice Reference Service, Department of Defense, Drug Enforcement Agency, Homeland Security, National Institutes of Health, Missouri State Highway Patrol, Kansas Bureau of Investigation, and so forth.

Employer record server 114 maintains, and provides access to, one or more employer database(s) 115 containing a patient's employment records. For example, employer database 115 can include a patient's employment status, attendance records, disciplinary notes, supervisory feedback, job performance notes, or any other employment data related to a patient. Financial record server 116 maintains, and provides access to, one or more financial record database(s) 117 containing financial data for a patient. For example, financial record database 115 can include a patient's credit rating, insurance claims, overall cash flow information, debit information, or any other financial data related to a patient.

Having identified various components of the operating environment 100, it is noted that any number of components may be employed to achieve the desired functionality within the scope of the present disclosure. Although the various components of FIG. 1 are shown with lines for the sake of clarity, in reality, delineating various components is not so clear, and metaphorically, the lines may more accurately be grey or fuzzy. Further, although some components of FIG. 1 are depicted as single components, the depictions are exemplary in nature and in number and are not to be construed as limiting for all implementations of the present disclosure. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Figure 2:
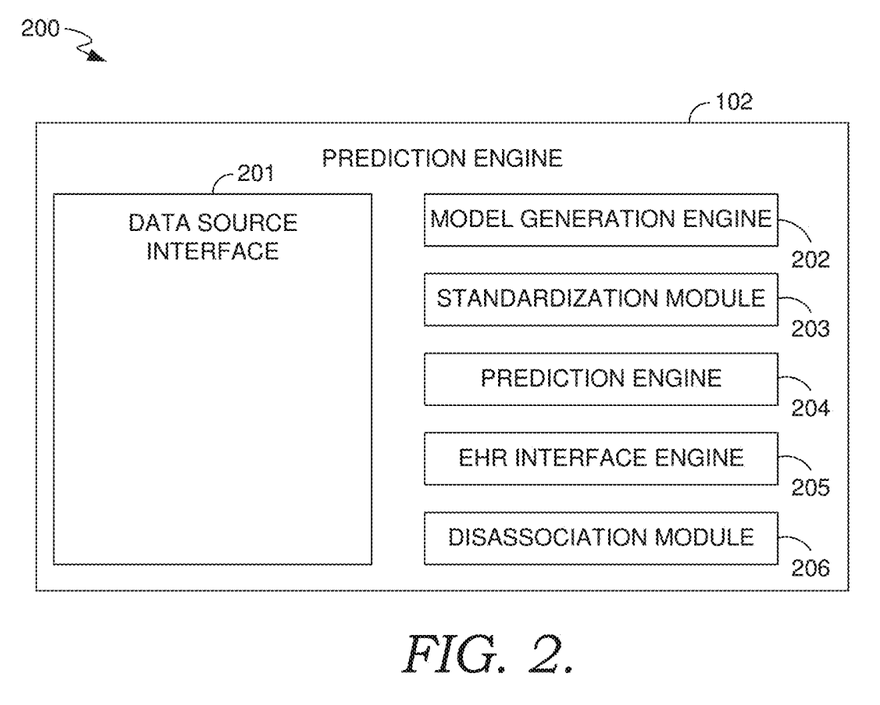
FIG. 2 depicts an exemplary prediction engine that facilitates predictions of a likelihood of addiction or relapse, in accordance with an embodiment of the disclosure.

Turning to FIG. 2, an example prediction engine 102 is depicted consistent with embodiments described herein. As mentioned above, prediction engine 102 generally facilitates acquisition and analysis of data from one or more disparate data sources relevant to the prediction of a patient's likelihood of addiction or relapse. Prediction engine 102 can include a data source interface 201, a model generation engine 202, a standardization module 203, a prediction engine 204, and EHR interface engine 205. In some embodiments, prediction engine 102 further includes a disassociation module 206.

The data source interface 201 facilitates retrieving and extracting database records, and cleaning the values of variables in records. For example, data source interface 201 can include an API library that includes specifications for routines, data structures, object classes, and variables that support the interaction of the prediction engine 102 architecture and the software framework of a plurality of disparate data sources (e.g., electronic health record server 104, prescription record server 106, academic record server 108, social media server 110, government agency record server 112, employer record server 114, financial record server 116, and so forth). Depending on which data source is being queried, or otherwise accessed, data source interface 201 utilizes the API library to tailor the query (or access request) to the corresponding data source. Further, in some embodiments, data source interface 201 performs functions for synonymic discovery, indexing or mapping variables in records, or mapping the disparate data source ontologies.

Model generation engine 202 generally facilitates generation and development of substance abuse and relapse prediction models. In some embodiments multiple models can be generated by model generation engine 202. For example, a model can be generated for an overall addiction or relapse score and a model can be generated for each class of pharmaceutical or drug with a documented potential for addiction. In this context, a pharmaceutical or drug class is used with its commonly understood meaning in the field. For example, morphine, heroine, hydrocodone, and oxycodone are opioids; alprazolam, clonazepam, diazepam, and estazolam are benzodiazepines; and so forth. Model generation engine 202 can also include a general addiction prediction model, which is developed to facilitate predictions of addiction or relapse if a class specific model produces a score outside of a predetermined range.

Continuing, model generation engine 202 uses historical records with known addiction or relapse statuses and machine learning techniques to generate and develop substance abuse and relapse prediction models in some embodiments. For example, a cohort of historical subjects in an electronic health records system with known addiction or relapse statuses can be identified. Known addiction and relapse statuses may be determined in a variety of ways. In some embodiments, for example, data source interface 201 may identify a plurality of subjects with documented addiction treatment events (such as admission to an addiction recovery program, treatment for an overdose, self-report, and similar events) or documented relapse events contained in the subject's electronic medical record. For example, blood/hair/urine/oral swab tests may indicate THC or its metabolites, opioids or their metabolites, and so on. In an embodiment, model generation engine 202 identifies subjects by ICD-9 diagnoses with a range indicative of substance use/addiction/treatment/relapse events. Model generation engine 202 then compiles the identified subjects into one or more cohorts. For example, model generation engine 202 can compile a cohort including all identified subjects, a second cohort including subjects with documented opioid addiction or relapse events, a third cohort including subjects with documented benzodiazepine addiction or relapse events, and so on. Notably, an individual subject can be included in multiple cohorts, such as the all identified subjects cohort and the opioid cohort. In some embodiments, model generation engine 202 retrieves historical values for treatment events, medication history, substance use history, physiologic values, demographic attributes, laboratory tests, or other features that are germane to treatment efficacy corresponding to each cohort subject. The historical values can be held as unstructured data, assembled into a temporal order, or both. Additionally, in some embodiments model generation engine 202 can access financial records and social media posts for each identified subject. In some embodiments, model generation engine 202 further de-identifies/anonymizes the subjects included in the cohort. Model generation engine 202 can use MANCOVA, support vector machine (SVM), Naïve Bayes, boosted and bagged decision trees, k-nearest neighbor, discriminant analysis, logistic regression, supervised learning, or any combination thereof to build a prediction model, identify input variables, and identify pre-model condition algorithms for each cohort. Further, model generation engine 202 can further identify input variables for the prediction model that reduce the likelihood of addiction. Said differently, some embodiments of model generation engine 202 determine the weights or relationships of the historical data that indicate potential addiction and the historical data that mitigates (or reduces) potential addiction.

Standardization module 203 generally conditions or otherwise prepares data based on inputs for prediction models generated by model generation engine 202. Standardization module 203 includes natural language processing services (not shown) such as Discern nCode™ developed by Cerner Corporation, or similar services. Further, standardization module 203 can load and execute operations or functions identified by the prediction model 204 for pre-model conditioning based on the information retrieved by data source interface 201. Additionally, standardization module 203 includes a data store, which in some embodiments includes data for a target patient (or information for multiple patients), including raw data sets or input variables; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, for example. It is contemplated that the term data includes any information that can be stored in a computer-storage device or system, such as user-derived data, computer usable instructions, software applications, or other information.

Prediction engine 204 generally, comprises the services or routines for forecasting likelihood of a target patient's addiction or relapse, which may be developed according to the method described in connection to model generation engine 202 and implemented in accordance with the methods described in connection to FIGS. 3 and 4. For example, prediction engine 204 performs statistical software operations, and can include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. The R-system modules or packages include, in an embodiment, MRsurv or survival packages, which may be utilized during model development for multiplicative-regression models for relative survival, and prodlim packages for performing product-limit estimation for censored event history analysis used in some implementations of the predictive model(s) for determining likelihood of relapse. Further, in some embodiments prediction engine 204 includes a multivariate analysis of covariance (MANCOVA) package or module, which may be utilized during model development for multi-dependent input variable identification and variable weighting.

EHR interface engine 206 generally facilitates access to the output of prediction engine 102 associated with a target patient. The EHR interface engine 205 can store the output (e.g., the substance abuse or relapse score) in the target patient's EHR, generate an alert visible when an authorized user accesses the target patient's EHR, generate and present an automatic alert coexistent with presentation of the determined likelihood of addiction, or any combination thereof. In some embodiments, EHR interface engine 205 prevents completion of a care provider action in the target patient's EHR until the substance abuse or relapse score is manually acknowledged. For example, in an embodiment, EHR interface engine 205 prevents finalization of a prescription in the target patient's EHR until the care provider acknowledges the substance abuse or relapse score or alert via a check box or popup that is displayed via care provider device 103.

Additionally, EHR interface engine 205 can modify any of the generated alerts by including mitigating input variables detected by prediction engine 102. Said another way, EHR interface engine 205 can, based on the model, include specific reference to any mitigating input variables (mitigation variable(s)) detected for the target patient in an alert. The mitigation alert can be included with substance abuse or relapse score, alert, or can be presented independently in some embodiments. For example, in an embodiment the mitigation alert can be provided coexistent with the substance abuse or relapse score.

In some embodiments, prediction engine 102 further comprises a disassociation module 206 that facilitates active disassociation of the input variables and conditioned inputs associated with a target patient. For example, disassociation module 206 can activate in response to a prediction model output and clear the target patient's locally stored data sets. The locally stored data sets include the input variables and the conditioned input variables retrieved by prediction engine 102 or received from the disparate data sources. Disassociating the data sets can include deleting the data sets from prediction engine's 102 local storage media, removing indications that the data sets are used as inputs into the particular prediction model, or otherwise obscuring the relationship between the data sets and prediction engine 102's output score.

In an embodiment, prediction engine 102 includes the services or routines, which may be embodied as one or more software agents or routines. Some embodiments of prediction engine 102 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of prediction engine 102 may further comprise one or more stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include multiple such stream processing services (in parallel, serially, or operating independently). Some embodiments of the invention also may be used in conjunction with Cerner Millennium®, Cerner CareAware® (including CareAware iBus®)), Cerner CareCompass®, or similar products and services.

Two illustrative examples are provided below in relation to FIGS. 3 and 4. Jane Doe, a Caucasian American teenager, is on the girls Lacrosse team and a member of the chess and Latin clubs at her high school. She suffered a leg injury during an out-of-town Lacrosse tournament several months ago and, among other things, was initially prescribed a week supply of a relatively low dose opioid-containing pharmaceutical by an emergency room physician. After a surgical repair of the injury at the hospital in Somewhere, Missouri (her home town), the surgeon prescribed a month supply (with one refill) of a higher dose opioid pharmaceutical. John Buck, an African American, is an Army Captain in his mid-thirties and was recently honorably discharged after two tours of active duty. During his last tour, John was hit in the leg with shrapnel from an explosion of a road side bomb. After moving back to Somewhere, Missouri he began to exhibit symptoms of post-traumatic stress disorder and suffers on-going leg pain related to his injury. Among other treatments, John's primary care physician prescribed an opioid and a psychiatrist prescribed a benzodiazepine-containing pharmaceutical. It will be understood by those skilled in the art that Jane and John are merely illustrative examples and not intended to limit the scope of any embodiments described herein. Further, Jane and John are not intended to represent actual patients; and as such, although they are used to assist explaining aspects of embodiments described herein, any similarity to an actual patient is merely coincidental.

Figure 3:
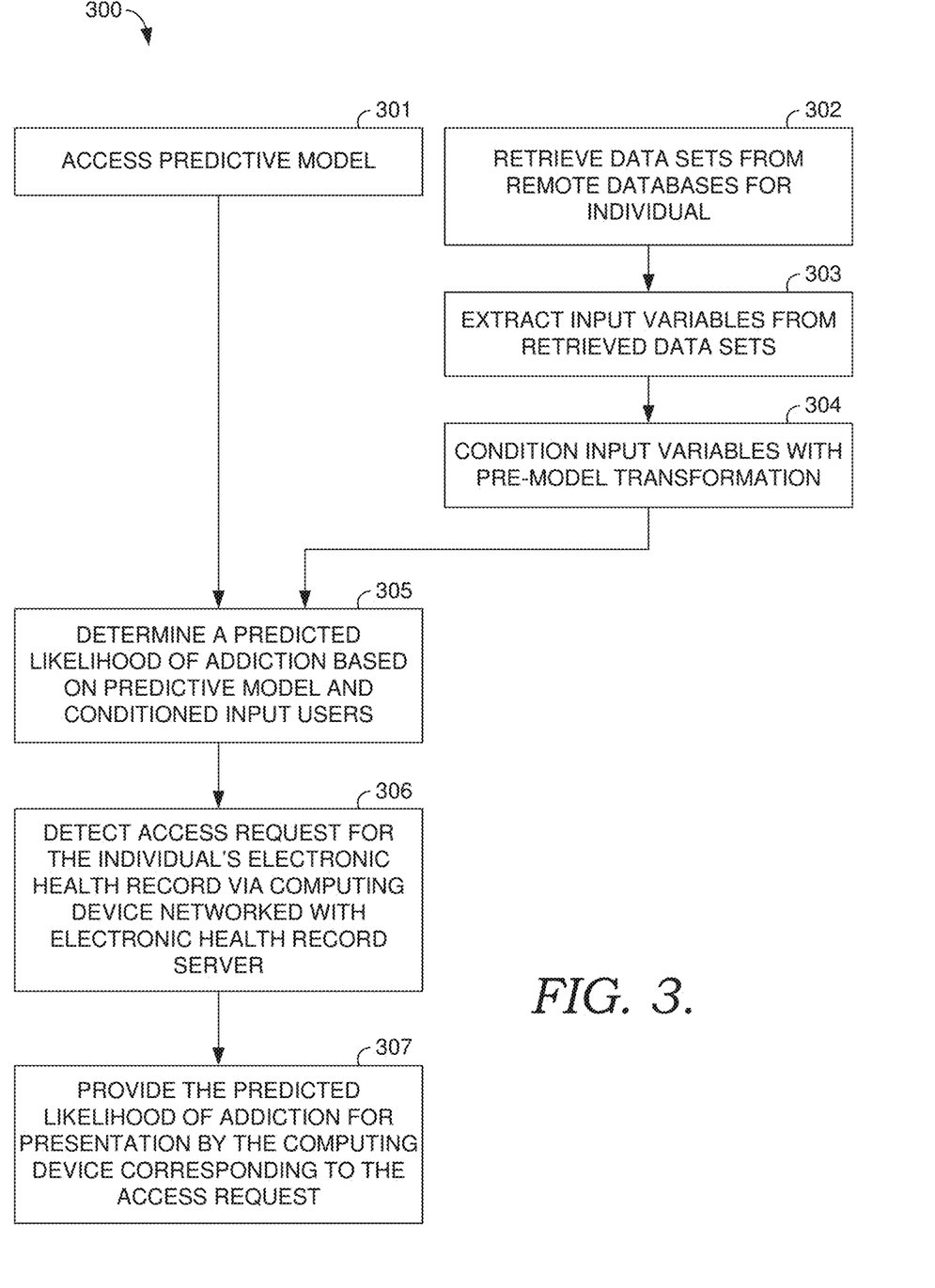
FIG. 3 depicts an exemplary method for predicting a likelihood of addiction or relapse for a target patient, in accordance with an embodiment of the disclosure.

With reference to FIG. 3 a method 300 for predicting a target patient's potential for addiction or relapse is provided consistent with embodiments described herein. Method 300 is facilitated by one or more components described in relation to FIGS. 1 and 2 in some embodiments. For example, a care provider can access prediction engine 102 via a care provider device 103 communicatively coupled to an EHR server 104. Input is communicated through a user interface presented by care provider device 103 identifying one or more patients for which a substance abuse prediction score is requested, the user interface can activate a prediction engine 102, and method 300 can begin at block 301 in some embodiments.

At block 301, a predictive model is accessed by prediction engine 102. The predictive model accessed by prediction engine 102 is a predetermined prediction model or a prediction model based on the target patient's data retrieved, received, or otherwise accessed by prediction engine 102. Additionally, alternatively, or concurrently, prediction engine 102 retrieves data sets from a plurality of remote data sources for the target patient at block 302. For example, during a post-surgery follow up appointment with her primary care provider (PCP), Jane's parent's consent to allow the PCP to use a substance abuse prediction score to assist the PCP to personalize Jane's recovery. The PCP identifies Jane's EHR as a target patient for prediction engine 102. Prediction engine 102 utilizes an API library to initialize communication with EHR server 104 associated with the out-of-town hospital, the EHR server 104 associated with the PCP's institution, a prescription record server 106, the academic record server(s) 108 corresponding to Jane's high school, the social media server(s) 110 associated with Jane's online presence, and government agency record server(s) 112. Similarly, and as another example, John consents to allow his PCP and his psychiatrist to use a substance abuse prediction score to assist with John's treatment. Prediction engine 102 utilizes an API library to initialize communication the EHR server 104 associated with the PCP's and psychiatrist's institutions, a prescription record server 106, the social media server(s) 110 associated with John's online presence, John's Army medical and service records (e.g., an EHR server 104, a governmental agency server 112, or a combination of both), and the employer server 114 maintaining John's employment records for his civilian job. The prediction engine(s) 102 retrieve the data sets associated with John and Jane maintained by each server. In some embodiments of method 300, prediction engine 102 communicates a request for a target patient's data to each remote server through network 101. The prediction engine 102 receives the target patient's data from the remote server(s) in response to the query request.

At block 303, prediction engine 102 extracts input variables from the retrieved data sets. The extracted variables include numeric and text information stored in the fields of the databases maintained by the remote databases accessed by the prediction engine 102. Further, in some embodiments of block 303 the prediction engine performs functions for synonymic discovery, indexing or mapping variables in the retrieved data sets to unify and normalize the information stored in fields from multiple servers of the same type. For example, synonymic discovery, indexing or variable mapping may be used for Jane to unify and normalize the EHR information retrieved from the out-of-town hospital and her PCP's institution. Further, synonymic discovery, indexing or variable mapping may be used for Jane to unify and normalize the social media posts, connections, and login activity where Jane has multiple accounts on different platforms. For another example, the prediction engine 102 can use synonymic discovery, indexing or variable mapping to unify and normalize the EHR information retrieved from John's Army medical record, his medical record associated with his PCP, and his medical record associated with his psychiatrist.

At block 304, prediction engine 102 conditions the input variables with pre-model transformations. Conditioning the input variables prior to providing the variables to the prediction model can reduce the computational burden of executing the prediction model. Additionally, conditioning the input variables can normalize the variables to the prediction model and thereby improve the flexibility of a given model (e.g., increasing the number of acceptable variable formats and improving the range of values the model is capable of evaluating). In some embodiments, the pre-model transformations applied by prediction engine 102 are based on the source of the input variables and determined during model generation by model generator 202. For example, conditioning governmental-derived input variables can be based on, in an illustrative example, data mining documentation indicating the availability, distribution and usage of illicit substances within the same geographic region as the target patient's current residence or the care provider's institution into an alphanumeric representation. Similarly, conditioning employer-derived input variables can be based on, in an illustrative example, data mining documentation indicating the target patient's (e.g., the employee's) employment status (such as "active", "on leave", "medical leave", "eligible for promotion", "terminated", or any other indication of the employee's status with the employer), attendance records (e.g., requested time off, "no-show" events, clock-in times, clock-out times, or any other indications of the employee's presence or absence), disciplinary notes (e.g. suspensions, probation, promotion, and so forth), supervisory feedback, job performance notes, or any other employment data related to the target patient.

For another example, in an embodiment, input variables from a social media server 110 can include text and images extracted by prediction engine 102. Prediction engine 102 can condition the input variables by utilizing image recognition to identify objects and people in the images. The identified objects can be transformed into text representing the identified objects. Further, prediction engine 102 can condition the text utilizing a customizable dictionary listing terms, phrases, colloquialisms, and slang used to identify pharmaceuticals and illicit substances (hereinafter collectively referred to as "markers"). The customizable dictionary can be automatically updated continuously, periodically, intermittently, or upon request. The frequency and the category of these markers used within a target patient's social media postings may be used by prediction engine 102 to transform the text (and text representing objects identified in images) into a pre-model value. In some embodiments, the text is provided to a semantic analysis model trained on historical social media records known to include a reference to a controlled substance or a substance listed in a potential-for-addiction formulary.

For example, John's social media posts may include an image of a case of beer and text that states "Man, we drank so much beer and wine last night I had to grab a ride home. I'll be popping Tylenol all day today to get rid of this hangover. Last time I go to a party on an empty stomach. Thank god for Tylenol and whoever took my keys! Also, who got my keys?" Prediction engine 102 may detect the case of beer in the image and transform the image to text "case of beer" or "beer"; further, the customizable dictionary may identify the markers "drank so much beer" with a weight of 1, "Tylenol" with a weight of 1 (used twice), "hangover" with a weight of 1, and "party" as a noun with a weight of 0. The total factor of this post and image can be transformed into a total of 4 (e.g., 1 from text representation of the image and 3 from the initial text). This process can be repeated by prediction engine 102 for each input variable from John's social media.

For another example, Jane's social media posts may include text that states "Man, been partying all week long and still buzzed off that kush. I think I have a future in that hydro game. I gotta get back in touch with my hook up!" Prediction engine 102 may utilize the customizable dictionary to identify the markers "been partying all week" with partying as a verb modified by the duration with a weight of 2, "still buzzed" with a weight of 1, "kush" with a weight of 2, "hydro game" with a weight of 2, "back in touch with my hook up" with a weight of 2. The prediction engine 102 can assign a total factor of this post with a transformed total of 9. This process can be repeated by prediction engine 102 for each input variable from Jane's social media.

Although some of the markers identified by prediction engine 102 in the illustrative examples could randomly appear in any social media posting, or may be used in a context unrelated to potential substance abuse; prediction engine 102 further conditions the social media input variables over a pre-determined range in some embodiments. For example, in an embodiment the predetermined range is a rolling four month interval beginning at a date determined by the target patient's initial relevant presentation documented in the EHR. Illustratively, in an example embodiment the final transformation for social media variables is conditioning the marker-based score for a given four month period with a value of 1 for 0-10 markers, 5 for 11-50 markers, and 10 for greater than 50 markers. In another embodiment, the predetermined range is customizable or weighted based on a time dependent clustering analysis.

Similarly, in some embodiments conditioning a target patient's EHR input variables is based on admission dates, symptomology, treatment, status, and other details about the target patient and treatment. For example, the EHR input variables can be chronologically ordered and analyzed. For Jane, the EHR input variables indicate a measurable change in her physiology which correlates to the initial Lacrosse injury. For example, the prediction engine 102 detects that Jane's weight and body mass index have fallen in each EHR entry since the injury. Further, Jane's blood work indicates detectable levels of pharmaceuticals or metabolites of pharmaceuticals that neither the PCP's EHR system nor the out-of-town hospital's EHR system has any record of prescriptions issued. The prediction engine 102 generates a pre-prediction model conditioned score for Jane's EHR-derived input variables of 10 based on the changes in weight and body mass index combined with evidence of prescribed medication. Similarly, prediction engine 102 conditions John's EHR-derived input variables and identifies a pre-prediction model conditioned score for John. The pre-model transformation indicates no significant change in weight or body mass index has happened for John and there is no evidence of unprescribed medication in John's blood work or urine analysis. Accordingly, the conditioned score for John is determined, by prediction engine 102, to be 0 for John's EHR-based input variables.

Further, in an example embodiment conditioning a target patient's Academic server-derived input variables is based on substantial decrease in overall grade point average (GPA), substantial increase in absenteeism, increase in disciplinary actions such as write ups, detention, and expulsion, decreased participation in school related activities such as sports, academic clubs/teams, social clubs, and the like. For an illustrative example, Jane maintained a grade point average between 88%-92% (or, on the common 4 point scale 3.52-3.68) for the past two years. In the two semesters since her injury a 5%-10% decrease in GPA is transformed to 1 point, an 11%-15% decrease is transformed to 2 points, and a decrease greater than 15% is transformed to 3 points. Similarly, Jane maintained 99% attendance for the past two years. In the past two semesters a 3%-5% decrease in attendance is transformed to 1 point, a 6%-10% decrease in attendance is transformed to 2 points, and a decrease in attendance greater than 10% is transformed to 3 points. Over the same time, if Jane dropped 1 and 2 activities 1 point is assigned and 2 points are given for decreased academic participations beyond 2 activities.

Yet still further, in an example embodiment conditioning a target patient's prescription record server-derived input variables is based on the date of prescription(s) (e.g., the date a care provider generated or signed a prescription); the fill date (e.g., the date the prescription was dispensed/"filled" by a pharmacy); the national drug code (NDC), generic name, or commercial name of the pharmaceutical; the amount and dosage of the pharmaceutical dispensed; and, the prescription notes (e.g., "take 2 pills every three hours", "PO BID", and so forth). The prescription record input variables can be conditioned by prediction engine 102 to identify the total aggregate days between controlled substance refills across the available timespan. For example, the prescription engine 102 can determine whether each prescribed pharmaceutical includes a controlled substance by querying the pharmaceutical formulary with the NDC or generic or non-generic name. Alternatively, in some embodiments, the target patient's prescription record server-derived input variables includes whether the prescription includes a controlled substance. Additionally, the fill dates of each prescription that includes a controlled substance can be ordered in a time series and the intervals between each fill can be calculated. Similarly, the prescription record input variables can be conditioned by prediction engine 102 to determine the total amount of controlled substance-containing pharmaceuticals dispensed from the first fill date to the penultimate fill date of the time series. Further, the prescription record input variables can be conditioned by prediction engine 102 to determine the aggregate prescribed dosage of the controlled substance over the time series from the first fill date to the penultimate fill date.

Continuing, the total aggregate days between controlled substance refills, total amount of controlled substance dispensed, and the aggregate prescribed dosage are compared in some embodiments. Based on the comparison a conditioned input variable for the model can be determined. In some embodiments, the comparison includes determining a ratio of the total amount of controlled substance dispensed and the aggregate prescribed dosage for the total aggregate time. Based on the ratio, the prediction engine 102 can classify the target patient's prescription record server-derived input variables as low, medium, or high risk for addiction or relapse. Based on the classification the conditioned input is generated as a numerical value for the prediction model. For example, Jane's prescription history indicates that over the past 100 days, 200 pills each containing 10 mg of a controlled substance have been dispensed, however the prescribed dosage indicates that only 100 pills at 10 mg are recommended by the care provider. Prediction engine 102 can determine the ratio for the total amount of controlled substance dispensed and the aggregate prescribed dosage for the total aggregate time as 2:1. Based on the model, a ratio of 2:1 is classified as medium risk and prediction engine 102 converts the ratio to a conditioned input variable of 5.

In another example, John's prescription history indicates that over the past 100 days, 300 pills each containing 10 mg of a controlled substance have been dispensed, however the prescribed dosage indicates that only 200 pills at 10 mg are recommended by the care provider. Prediction engine 102 can determine the ratio for the total amount of controlled substance dispensed and the aggregate prescribed dosage for the total aggregate time as 3:2. Based on the model, a ratio of 3:2 is also classified as medium risk and prediction engine 102 converts the ratio to a conditioned input variable of 5. Similarly, in some embodiments, a ratio of 1:1 or less is classified as low risk and converted to a conditioned input variable of 1; a ratio greater than 1:1 but less than 3:1 is classified as medium risk and converted to a conditioned input variable of 5; and, a ratio greater than or equal to 3:1 is classified as high risk and converted to a conditioned input variable of 10. However, one skilled in the art will understand that conditioning a target patient's prescription record server-derived input variables can vary based on the particular model generated by a model generation engine, such as model generation engine 202.

At block 305, a predicted likelihood of addiction or relapse is determined. In some embodiments, the predicted likelihood is based on the predictive model and the conditioned input from block 304. For example, a model can account for the conditioned inputs retrieved for the target patient and provided as input to the model. In an example embodiment, the model ratio-scales the conditioned inputs based on the model's expected input variables and the available input variables for the target patient. For example, where all of the expected inputs were retrieved from the disparate data sources the model can have a maximum score of 100 wherein an output score of 1-25 indicates no evidence of dependency or relapse, 26-50 indicates possible evidence of dependency or relapse, 51-75 indicates moderate likelihood of dependency or relapse, and 76-100 indicates severe likelihood of dependency or relapse. In another illustrative example, where half of the expected inputs were retrieved for the model, the maximum score is scaled to 50 wherein an output score of 1-12 indicates no evidence of dependency or relapse, 13-23 indicates possible evidence of dependency or relapse, 24-38 indicates moderate likelihood of dependency or relapse, and 29-50 indicates a severe likelihood of dependency or relapse. In an embodiment, the prediction score is compared to a customizable risk threshold. When the output score exceeds the customizable risk threshold, an addiction or relapse alert is generated. In some embodiments, the output of the prediction model is stored in the target patient's EHR. Additionally, in an embodiment, the input variables and the conditioned input variables are deleted, removed, or otherwise disassociated from the target patient's output (e.g., the predicted likelihood of addiction or relapse) stored by prediction engine 102. Conventional modeling techniques store these input variables and conditioned input variables for post model evaluation. However, disassociating the data prevents post-hoc rationalization by the target patient, the care provider, or a target patient's guardian(s). Further, disassociating the data prevents the target patient from intentionally altering or attempts to alter the input variables in situations where prediction engine 102 is used at a future time point to generate a second predicted likelihood of addiction or relapse for the target patient.

At block 306, an access request for the target patient's electronic health record via a computing device communicatively coupled with the electronic health record system server is detected. The request can be a request to submit a prescription for the target patient or create a prescription for the target patient by the caregiver via the computing device networked with the remote health record server. Additionally, the request can be an imbedded action coded into any action during the use of the electronic health record system server. In response to the access request, at block 307 the substance abuse and relapse score may be provided to an appropriate care provider associated with the access request for the target patient. In an embodiment, an alert may be issued and the prediction information may be utilized for automatically scheduling an intervention or otherwise modifying a prescription for the target patient. For example, the substance abuse or relapse prediction alert may be presented to the caregiver via the computing device coexistent with presentation of the determined likelihood of addiction. In some embodiments, the alert can suggest increasing monitoring, alternative pharmaceutical combinations, discussing the score with the target patient, or other treatment regimes, for example. In some embodiments, the prediction may be stored and compared against future risk-of-relapse predictions to determine whether a patient's risk has changed.

Figure 4:
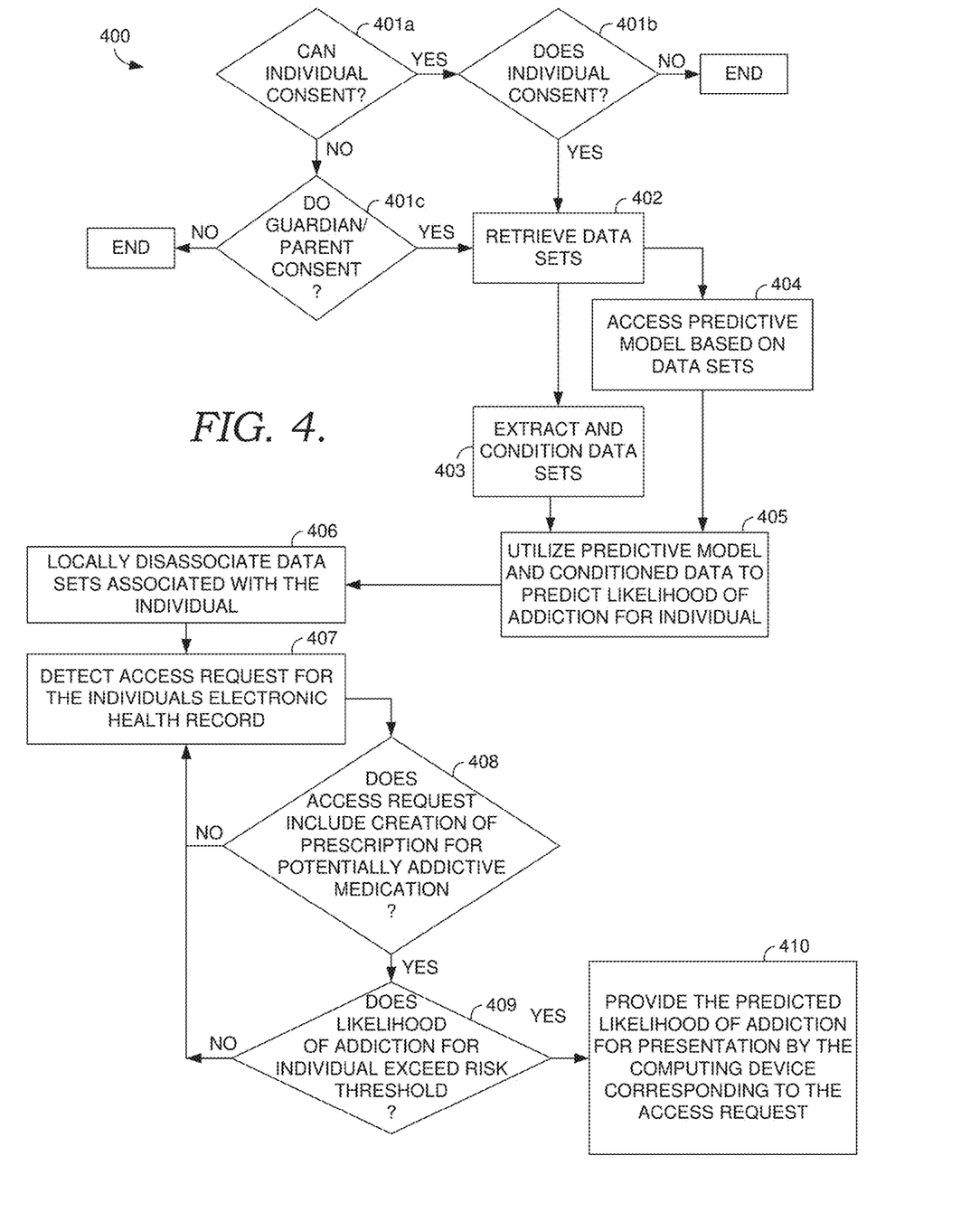
FIG. 4 depicts another exemplary method for predicting a likelihood of addiction or relapse for a target patient, in accordance with an embodiment of the disclosure; and, FIG. 5 depicts an example computing device, in accordance with an embodiment of the disclosure.

Turning to FIG. 4, another example method 400 is provided for determining a likelihood of addiction or relapse for a target patient in accordance with embodiments described herein. Some embodiments of method 400 can be facilitated by one or more prediction engines, such as prediction engine 102. Accordingly, some embodiments of method 400 begins at block 401a, wherein prediction engine 102 determines if a target patient is able to consent for enrollment. If the target patient is beyond the age of majority, or otherwise has the capacity to consent to enrollment, block 401a proceeds to block 401b. For example, prediction engine 102 mines the EHR for the target patient and determines the target patient's age or legal status. If the target patient's age exceeds, for illustrative example, 18 or the target patient's EHR contains a record of legal authority to consent, enrollment block 401a proceeds to block 401b. Otherwise, prediction engine 102 determines that the target patient does not have capacity to consent and block 401a proceeds to block 401c.

At block 401b, prediction engine 102 determines if the target patient consents for evaluation by the prediction of a likelihood for addiction or relapse. In some embodiments, the care provider's device 103 displays an enrollment consent form that can be provided to the target patient for review and acceptance or refusal. If the target patient refuses to consent method 400 ends. If the target patient accepts, block 401b proceeds to block 402. Similarly, at block 401c, the care provider's device 103 displays an enrollment consent form that can be provided to the target patient's guardian(s) or parent(s) for review and acceptance or refusal. If the target patient's guardian(s) or parent(s) refuses to consent method 400 ends. If the target patient accepts, block 401c proceeds to block 402.

At block 402, prediction engine 102 retrieves data sets from a plurality of remote data sources for the target patient at block 302. For example, prediction engine 102 utilizes an API library to initialize communication with one or more EHR servers 104, one or more prescription record servers 106, one or more academic servers 108, one or more social media servers 110, one or more government agency servers 112, one or more employer servers 114, one or more financial servers 116, or any combination thereof. In some embodiments of method 400, prediction engine 102 communicates a request for a target patient's data to each remote server through network 101. The prediction engine 102 receives the target patient's data from the remote servers in response to the request. In some embodiments, prediction engine 102 can perform block 403 and block 404 in parallel (e.g., concurrently) or in series after the data sets are retrieved. However, it will be understood by those skilled in the art that where blocks 403 and 404 are performed in series either block 403 or block 404 can be performed first.

At block 403, prediction engine 102 extracts input variables from the retrieved data sets. The extracted variables include numeric and text information stored in the fields of the databases maintained by the remote databases accessed by the prediction engine 102. Further, in some embodiments of block 403 the prediction engine performs functions for synonymic discovery, indexing or mapping variables in the retrieved data sets to unify and normalize the information stored in fields from multiple servers of the same type.

At block 404, a predictive model is accessed by prediction engine 102. The predictive model accessed by prediction engine 102 is a predetermined prediction model or a prediction model based on the target patient's data retrieved, received, or otherwise accessed by prediction engine 102 from block 402.

At block 405, prediction engine 102 conditions the input variables with pre-model transformations and utilizes the predictive model to predict a likelihood of addiction or relapse for a target patient. Conditioning the input variables prior to providing the variables to the prediction model can reduce the computational burden of executing the prediction model. Additionally, conditioning the input variables can normalize the variables to the prediction model and thereby improve the flexibility of a given model (e.g., increasing the number of acceptable variable formats and improving the range of values the model is capable of evaluating). In some embodiments, the pre-model transformations applied by prediction engine 102 are based on the source of the input variables and determined during model generation by model generation engine 202. Further, a predicted likelihood of addiction or relapse is determined based on the predictive model and the conditioned input variables. For example, a model can account for the conditioned inputs retrieved for the target patient and provided as input to the model. In an example embodiment, the model ratio-scales the conditioned inputs based on the model's expected input variables and the available input variables for the target patient.

At block 406, the locally stored data sets associated with the target patient are disassociated. The locally stored data sets include the input variables and the conditioned input variables retrieved by prediction engine 102 or received from the disparate data sources. Disassociating the data sets can include deleting the data sets from prediction engine's 102 local storage media, removing indications that the data sets are used as inputs into the particular prediction model, or otherwise obscuring the relationship between the data sets and prediction engine 102's output score.

At block 407, an access request for the target patient's electronic health record via a computing device communicatively coupled with the electronic health record system server (such as care provider device 103) is detected. The request can be a request to submit a prescription for the target patient or create a prescription for the target patient by the caregiver via the computing device networked with the remote health record server. Additionally, the request can be an imbedded action coded into any action during the use of the electronic health record system server. At block 408, the prediction engine 102 determines if the access request includes creation of a prescription for a potentially addictive medication. For example, EHR interface engine 202 detects the creation of a prescription in the target patient's EHR for a pharmaceutical comprising an opioid, barbiturate, benzodiazepine, phenidate, amphetamine, and other controlled substance. If the access request does not include creation of a prescription or the prescription does not include a potentially addictive medication block 408 returns to block 407, in some embodiments.

Continuing, where an access request including a prescription for a potentially addictive medication is detected at block 408, the method 400 proceeds to block 409, wherein the predicated likelihood of addiction or relapse is compared to a risk threshold. Where the predicated likelihood of addiction or relapse does not exceed the risk threshold, indicating an insignificant risk of addiction, block 409 returns to block 407. Where the predicated likelihood of addiction or relapse exceeds the risk threshold, indicating a significant risk of addiction, block 409 proceeds to block 410.

At block 410, an alert is presented to the care provider via care provider device 103. The alert can include the substance abuse and relapse score and may be provided to an appropriate care provider associated with the access request for the target patient. In an embodiment, an alert may be issued; the prediction information may be utilized for automatically scheduling an intervention or otherwise modifying a prescription for the target patient. For example, the substance abuse or relapse prediction alert may be presented to the caregiver via the computing device coexistent with presentation of the determined likelihood of addiction. In some embodiments, the alert can suggest increasing monitoring, alternative pharmaceutical combinations, discussing the score with the target patient, or other treatment regimes, for example. In some embodiments, the prediction may be stored and compared against future risk-of-relapse predictions to determine whether a patient's risk has changed.

Figure 5:
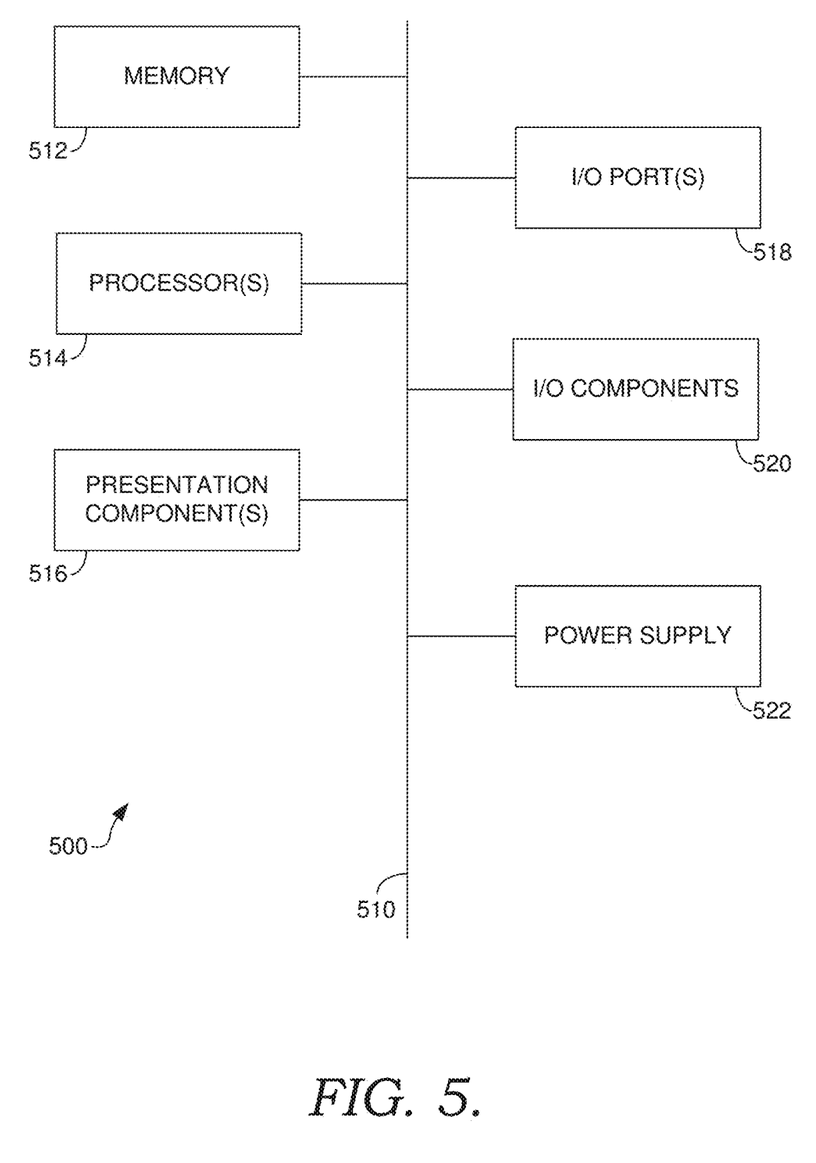

Having described an overview of embodiments of the present invention, an exemplary operating environment in which embodiments of the present invention may be implemented is described below in order to provide a general context for various aspects of the present invention. Referring to FIG. 5 in particular, an exemplary operating environment for implementing embodiments of the present invention is shown and designated generally as computing device 500. Computing device 500 is but one example of a suitable computing environment and is not intended to suggest any limitation as to the scope of use or functionality of the invention. Neither should the computing device 500 be interpreted as having any dependency or requirement relating to any one or combination of components illustrated.

The invention may be described in the general context of computer code or machine-useable instructions, including computer-executable instructions such as program modules, being executed by a computer or other machine, such as a personal data assistant or other handheld device. Generally, program modules including routines, programs, objects, components, data structures, etc. refer to code that perform particular tasks or implement particular abstract data types.

The invention may be practiced in a variety of system configurations, including hand-held devices, consumer electronics, general-purpose computers, more specialty computing devices, etc. The invention may also be practiced in distributed computing environments where tasks are performed by remote-processing devices that are linked through a communications network.

With reference to FIG. 5, computing device 500 includes a bus 510 that directly or indirectly couples the following devices: memory 512, one or more processors 514, one or more presentation components 516, input/output ports 518, input/output components 520, and an illustrative power supply 522. Bus 510 represents what may be one or more busses (such as an address bus, data bus, or combination thereof). Although the various blocks of FIG. 5 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. We recognize that such is the nature of the art, and reiterate that the diagram of FIG. 5 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 5 and reference to "computing device."

Computing device 500 typically includes a variety of computer-readable media. Computer-readable media can be any available media that can be accessed by computing device 500 and includes both volatile and nonvolatile media, removable and non-removable media. By way of example, and not limitation, computer-readable media may comprise computer storage media and communication media.

Computer storage media include volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 500. Computer storage media excludes transitory signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 512 includes computer storage media in the form of volatile and/or nonvolatile memory. The memory may be removable, non-removable, or a combination thereof. Exemplary hardware devices include solid-state memory, hard drives, optical-disc drives, etc. Computing device 500 includes one or more processors that read data from various entities such as memory 512 or I/O components 520. Presentation component(s) 516 present data indications to a user or other device. Exemplary presentation components include a display device, speaker, printing component, vibrating component, etc.

I/O ports 518 allow computing device 500 to be logically coupled to other devices including I/O components 520, some of which may be built in. Illustrative components include a microphone, joystick, game pad, satellite dish, scanner, printer, wireless device, etc.

Embodiments described in the paragraphs above may be combined with one or more of the specifically described alternatives. In particular, an embodiment that is claimed may contain a reference, in the alternative, to more than one other embodiment. The embodiment that is claimed may specify a further limitation of the subject matter claimed.

The subject matter of embodiments of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

I claim:

1. A method for automatically predicting a likelihood of addiction for an individual based on a predictive model, the method comprising:

accessing a predictive model having a plurality of input variables;

retrieving a plurality of sets of structured data for the individual via at least one application programing interface, wherein each set of structured data of the plurality of sets of structured data is retrieved from a remote disparate database, wherein at least one set of structured data of the plurality of sets of structured data is received from an academic record server, an employment record server, or a financial record server, wherein the academic record server maintains and provides access to one or more academic databases containing school records for the individual;

extracting from each retrieved set of structured data a set of input variables;

automatically standardizing the set of input variables, using a pre-model transformation to generate standardized input variables;

utilizing the predictive model and the standardized input variables to determine a prediction for the likelihood of addiction for the individual, wherein the prediction for the likelihood of addiction for the individual is based on the at least one set of structured data of the plurality of sets of structured data received from the academic record server, the employment record server, or the financial record server;

detecting an access request for an electronic health record (EHR) of the individual by a caregiver via a computing device networked with a remote health record server maintaining the individual's EHR; and in response to detecting the access request for the individual's electronic health record (EHR), providing the determined likelihood of addiction for presentation to the caregiver via the computing device, wherein in response to the likelihood of addiction for the individual exceeding a risk threshold an automatically generated alert is presented coexistent with presentation of the determined likelihood of addiction, the automatically generated alert preventing execution of the access request until an input is received via the computing device that corresponds to acknowledgment of the caregiver of the automatically generated alert.

2. The method of claim 1, further comprising:
storing the prediction for the likelihood of addiction in the individual's EHR maintained by the remote health record server.

3. The method of claim 2, wherein in response to utilizing the predictive model and the standardized input variables to determine the likelihood of addiction for the individual, the standardized input variables and the set of input variables are locally disassociated from the prediction for the likelihood of addiction and disassociated from the individual's EHR.

4. The method of claim 1, wherein the predictive model is trained with an anonymized dataset comprising a plurality of known cases of addiction.

5. The method of claim 1, wherein the pre-model transformation comprises generating an alphanumeric representation of an extracted input variable.

6. The method of claim 1, wherein the access request for the individual's EHR comprises creation of a prescription for the individual by the caregiver via the computing device networked with the remote health record server.

7. The method of claim 6, further comprising:
determining that the likelihood of addiction for the individual exceeds a risk threshold; and
providing an automatically generated alert for presentation to the caregiver via the computing device coexistent with presentation of the determined likelihood of addiction.

8. The method of claim 7, wherein the automatically generated alert prevents completion of the prescription for the individual until manually acknowledged by the caregiver via the computing device networked with the remote health record server.

9. The method of claim 1, wherein the plurality of sets of structured data are retrieved from another of:
a social media platform,
an academic record server,
an employment record server,
a remote health history server,
a financial record server, or
a governmental server.

10. The method of claim 1, wherein a first set of structured data of the plurality of structured data is received from the academic server, a second set of structured data of the plurality of sets of structured data is received from, the employment record server and a third set of structured data of the plurality of structured data is received from the financial record server.

11. The method of claim 1, wherein the at least one set of structured data of the plurality of sets of structured data is received from the employment record server wherein the employment record server maintains and provides access to one or more employer databases including employment records for the individual.

12. The method of claim 1, wherein the academic record server is a remote educational institution server.

13. The method of claim 1, wherein in response to utilizing the predictive model and the standardized input variables to determine the likelihood of addiction for the individual, the standardized input variables and the set of input variables are locally disassociated from the prediction for the likelihood of addiction and disassociated from the individual's EHR.

14. The method of claim 1, wherein the at least one set of structured data of the plurality of sets of structured data is received from the financial record server, wherein the financial record server maintains and provides access to one or more financial record databases containing financial data for the individual.

15. One or more non-transitory computer readable storage media storing computer executable instructions, the instructions being executable by one or more processors to perform operations comprising:
accessing a predictive model having a plurality of input variables;
retrieving a plurality of sets of structured data for an individual, wherein each set of structured data of the plurality of sets of structured data is retrieved from a remote disparate database, wherein at least one set of structured data of the plurality of sets of structured data is received from a remote academic record server, a remote employment server, or a remote financial record server, wherein the academic record server maintains and provides access to one or more academic databases containing school records for the individual;
extracting from each set of structured data a set of input variables;
automatically standardizing the set of input variables using a pre-model transformation to generate standardized input variables, the pre-model transformation based on the remote disparate database from which the structured data was retrieved;
utilizing the predictive model and the standardized input variables to determine a prediction for a likelihood of addiction for the individual, wherein the prediction for the likelihood of addiction for the individual is based on the at least one set of structured data of the plurality of sets of structured data received from the academic record server, the employment record server, or the financial record server;
detecting an access request for an electronic health record (EHR) of the individual by a caregiver via a computing device networked with a remote health record server maintaining the individual's EHR; and
in response to detecting the access request for the individual's electronic health record (EHR), providing the determined likelihood of addiction for presentation to the caregiver via the computing device, wherein in response to the determined likelihood of addiction for the individual exceeding a risk threshold an automatically generated alert is presented coexistent with presentation of the determined likelihood of addiction, the automatically generated alert preventing execution of the access request until a predefined input that corresponds to acknowledgment of the automatically generated alert is received via the computing device.

16. The non-transitory computer readable storage media of claim 15, wherein the access request for the individual's EHR comprises creation of a prescription for the individual by the caregiver via the computing device networked with the remote health record server, and wherein the computer instructions further cause the computer to perform operations comprising:
determining that the determined likelihood of addiction for the individual exceeds a risk threshold; and providing an automatically generated alert for presentation to the caregiver via the computing device coexistent with presentation of the determined likelihood of addiction.

17. The non-transitory computer readable storage media of claim 16, wherein the automatically generated alert prevents the computing device creating the prescription from adding the prescription to the individual's EHR until manually acknowledged by the caregiver via the computing device networked with the remote health record server.

18. The non-transitory computer readable storage media of claim 16, wherein the computer instructions further cause the computer to perform operations comprising:
    detecting a prescribed substance within the prescription for the individual; and
    determining the prescribed substance is within a potential-for-addiction formulary.

19. The non-transitory computer readable storage media of claim 15, wherein the computer instructions further cause the computer to perform operations comprising:
    storing the prediction for the likelihood of addiction in the individual's EHR maintained by the remote health record server; and
    in response to utilizing the predictive model and the standardized input variables to determine the likelihood of addiction for the individual, disassociating the standardized input variables and the sets of input variables from the prediction for the likelihood of addiction.

20. The non-transitory computer readable storage media of claim 15, wherein the computer instructions further cause the computer to perform operations comprising:
    extracting from at least one set of retrieved structured data an addiction mitigation variable; and
    providing an automatically generated mitigation alert for presentation to the caregiver via the computing device coexistent with presentation of the determined likelihood of addiction, the mitigation alert comprising an indication of the addiction mitigation variable.

21. The non-transitory computer readable storage media of claim 15, wherein at least one of the plurality of sets of structured data comprises at least one of hospital admission dates, symptomology, treatment, or status.

22. The non-transitory computer readable storage media of claim 15, wherein at least one of the plurality of sets of structured data comprises free text, and wherein the corresponding pre-model transformation comprises:
    accessing a semantic analysis model, wherein the free text from the at least one of the sets of structured data is an input into the semantic analysis model, and an output of the semantic analysis model comprises at least a portion of the standardized input variables.

23. The non-transitory computer readable storage media of claim 22, wherein the semantic analysis model is trained on historical social media records known to include a reference to a controlled substance.

24. A system for predicting a likelihood of addiction for an individual based on a predictive model, the system comprising:
    one or more processors;
    a storage device storing a computer program product comprising computer instructions that, upon execution by the one or more processors, cause the one or more processors to perform operations comprising:
        accessing a predictive model having a plurality of input variables;
        retrieving an electronic health record (EHR) from a remote health record server, the EHR corresponding to the individual and including structured data;
        retrieving a set of social media records from a remote media server, the set of social media records corresponding to the individual;
        retrieving a set of personnel records from a remote personnel sever, the set of personnel records corresponding to the individual;
        retrieving a set of academic records from a remote educational institution server, the set of academic records corresponding to the individual, wherein the remote educational institution server maintains and provides access to one or more academic databases containing school records for the individual;
        extracting a first set of input variables from the EHR, a second set of input variables from the set of social media records, and a third set of input variables from the set of academic records;
        automatically standardizing the first set of input variables, the second set of input variables, and the third set of input variables using a set of pre-model transformations to generate standardized input variables;
        utilizing the predictive model and the standardized input variables to determine a prediction for a likelihood of addiction for the individual, wherein the prediction for the likelihood of addiction for the individual is based on the first set of input variables from the EHR, the second set of input from the set of social media records, and the third set of input variables from the set of academic records;
        determining that the determined likelihood of addiction for the individual exceeds a risk threshold;
        detecting a creation of a prescription for the individual by a caregiver via a computing device networked with the remote health record server; and
        in response to the determined likelihood of addiction for the individual exceeding the risk threshold and the detection of creation of a prescription for the individual by the caregiver via a computing device networked with the remote health record server, providing the determined likelihood of addiction and an automatically generated alert for coexistent presentation to the caregiver via the computing device, wherein the automatically generated alert prevents the computing device creating the prescription from adding the prescription to the EHR until manually acknowledged by the caregiver via the computing device networked with the remote health record server.

25. The system of claim 24, wherein the second set of input variables comprises free text, and wherein the set of pre-model transformations comprises:
    providing a semantic analysis model with the free text as an input, the semantic analysis model trained on historical social media records known to include a reference to a controlled substance, and wherein an output of the semantic analysis model comprises at least a portion of the standardized input variables.

* * * * *